United States Patent
Lin (10) Patent No.: US 9,585,729 B2
(45) Date of Patent: Mar. 7, 2017

(54) DRILL GUIDE DEVICE FOR DENTAL IMPLANT

(71) Applicant: Hsieh-Hsing Lin, New Taipei (TW)

(72) Inventor: Hsieh-Hsing Lin, New Taipei (TW)

( * ) Notice: Subject to any disclaimer, the term of this patent is extended or adjusted under 35 U.S.C. 154(b) by 208 days.

(21) Appl. No.: 14/560,664

(22) Filed: Dec. 4, 2014

(65) Prior Publication Data

US 2016/0157960 A1    Jun. 9, 2016

(51) Int. Cl.
*A61C 1/08*    (2006.01)

(52) U.S. Cl.
CPC ............... *A61C 1/084* (2013.01); *A61C 1/082* (2013.01); *A61C 1/085* (2013.01)

(58) Field of Classification Search
CPC .......... A61C 1/082; A61C 1/084; A61C 1/085
USPC ............................................... 433/72, 74–76
See application file for complete search history.

(56) References Cited

U.S. PATENT DOCUMENTS

| 2009/0286197 A1* | 11/2009 | Jamison | A61C 1/084 433/75 |
| 2009/0298008 A1* | 12/2009 | Groscurth | A61C 1/084 433/74 |
| 2010/0185201 A1* | 7/2010 | Kim | A61C 1/12 606/80 |

* cited by examiner

*Primary Examiner* — Michael Carey (57) ABSTRACT

A drill guide device for dental implant has a positioning unit and a guiding unit. The positioning unit has a rod, a twist knob and a base. The twist knob has a first indexing table and at least two graduated markings of elevation angle. The base has a second indexing table matching the first indexing table. The twist knob is mounted in the base. The guiding unit has an inner guider and a middle guider. The inner guider has a first bending portion and two first abutting panels, and an inner diameter of the first bending portion corresponds to an outer diameter of the rod. The middle guider has a second bending portion and two second abutting panels respectively attached to the first abutting panels, and an inner diameter of the second bending portion corresponds to an outer diameter of the first bending portion.

6 Claims, 8 Drawing Sheets

DRILL GUIDE DEVICE FOR DENTAL IMPLANT

BACKGROUND OF THE INVENTION

1. Field of the Invention

The present invention relates to a drill guide device, especially a drill guide device for dental implant that can improve efficiency of fabricating a surgical stent.

2. Description of the Prior Arts

Teeth are calcified structure formed in the mouth for biting and chewing. Adult's teeth may be damaged by oral diseases or external forces, and the broken teeth are unable to regenerate. After the teeth are damaged, the alveolar bone and the gums of the mouth may be shrunk, and this may impair the eating capability. To avoid the above-mentioned problem, the common treatment is dental implant to replace the broken or lost teeth with artificial teeth.

Dental implant is done by first drilling a pilot hole in suitable size on the dental ridge of a patient, and planting an implant fixture into the pilot hole of the dental ridge. After the dental ridge is healed, an abutment is securely connected to the implant fixture, and finally a crown is mounted around the abutment to finish the implant. The crown is supported by the implant fixture and the dental ridge to sustain the forces of chewing and biting, so the eating function is regained.

The dental implant comprises multiple steps, and the first step is obtaining implantology data by computerized tomographic scan and manufacturing the gum model of a patient, the second step is drilling a hole in the gum model and producing a surgical stent. Implant site and angulation have to be confirmed by scan and modified by the dentist based on the actual diagnosis. For example, if bone under the original drill site is damaged or thin, a new drilling of the hole needs to avoid the site of the thin dental bone and move to another site with thick dental bone in consideration of the patent's teeth to bear the pressure on the vertical and horizontal directions, such that the implant fixture and the crown can sustain the biting forces from the mouth; or the dentist needs to do some bone grafting to augment the bone volume thus to keep the ideal position for restoration. It means that the appropriate drilling site, orientation and angulation are the key factors to successful dental implant.

Figure 7:
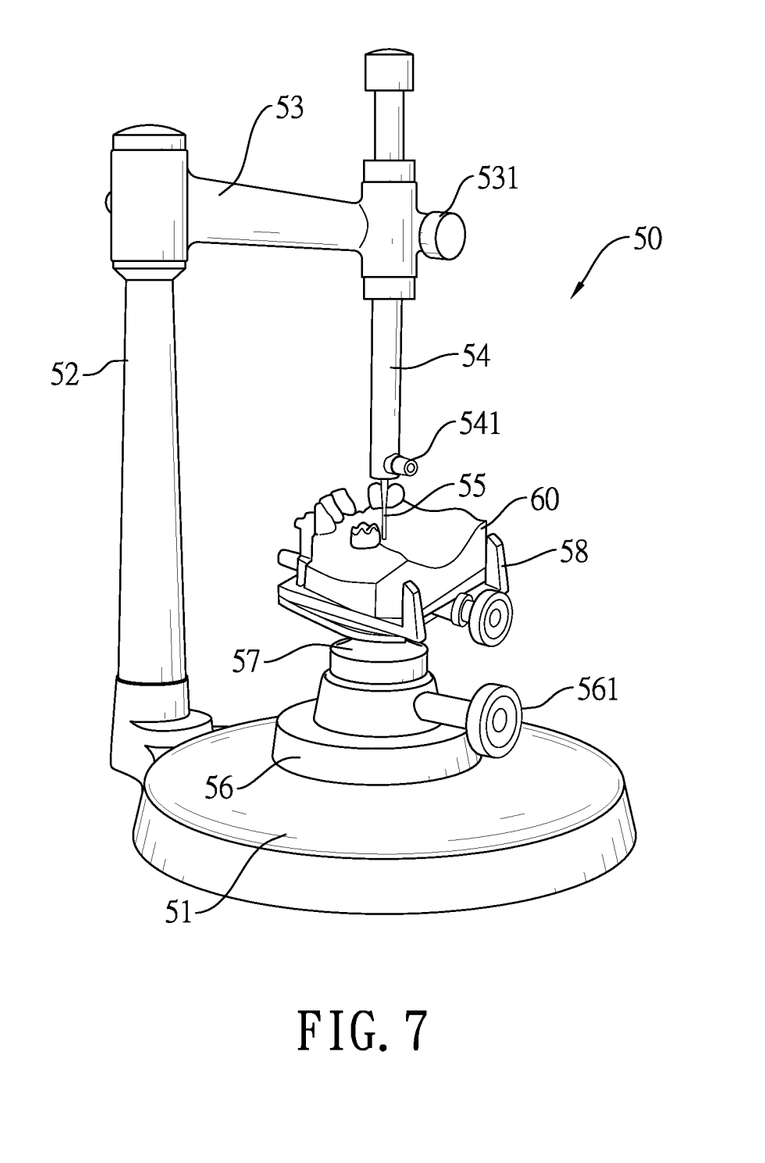
FIG. 7 is an operating view of a surveyor in accordance with the prior art.

A conventional technique for making surgical stent uses a standard rod and multiple guiders in different diameters. In the fabrication process, the dentist first drills on an implant site on the gum model according to the implantology data obtained by pre-surgical scan and computation, and mounting the standard rod into a hole drilled on the implant site. With reference to FIG. 7, the gum model is clamped securely by a surveyor 50 for confirming the orientation and elevation angle of the standard rod. The surveyor 50 has a base platform 51, a pillar 52, a horizontal arm 53, a vertical arm 54, a reference rod 55, a supporting seat 56, a universal joint 57 and a cast holder 58. The pillar 52 is mounted on and protrudes from one side of the base platform 51, the horizontal arm 53 is mounted on a top end of the pillar 52, and the vertical arm 54 is mounted through the horizontal arm 53 and corresponds to a center of the base platform 51.

The reference rod 55 is mounted on a bottom end of the vertical arm 54. The horizontal arm 53 has a first knob 531 for adjusting the height of the vertical arm 54. The vertical arm 54 has a second knob 541 for fixing the reference rod 55. The supporting seat 56 is mounted on the center of the base platform 51 below the vertical arm 54, the universal joint 57 is mounted on the supporting seat 56, and the cast holder 58 is connected to the universal joint 57. The cast holder 58 is applied to hold a gum model 60, and the universal joint 57 can be turned for adjusting the elevation angle of the cast holder 58 relative to the reference rod 55.

The elevation angle of the standard rod is measured by the surveyor 50 for confirming the orientation and elevation angle of the standard rod, and if the orientation or elevation angle of the standard rod is incorrect, the hole of the gum model has to be re-drilled and the measuring steps are repeated, which causes a complicated procedure in drilling and measuring. When the orientation and elevation angle are correct, multiple guiders are mounted on the standard rod. The number of the guiders depends on the actual diagnosis. The diameter of the biggest guider is the actual size of the hole to be drilled on the dental ridge of the patient.

Then, the gum model, the standard rod, and the multiple guiders are covered by resin. After a while, the resin is solidified to form a surgical stent. By removing the standard rod from the surgical stent, the surgical stent is mounted on the dental ridge of the patient for processing the drilling.

The conventional standard rod is mounted in the gum model, and the gum model has to be mounted securely on the surveyor for confirming the orientation and elevation angle of the standard rod, and then continuing the process of fabricating the surgical stent. As each tooth of the patient has a unique elevation angle, when a patient needs to install multiple dental implants, multiple measuring and readjusting steps are needed before mounting the standard rods into the gum model. This causes a complicated process and takes lots of time to fabricate the surgical stent. After mounting the standard rods into the gum model, the drilling site, orientation and angulation of the gum model need to be confirmed by the oral scan data of the patient. So for improving the efficiency of fabricating the surgical stent, simplifying the measuring steps is necessary.

To overcome the shortcomings, the present invention provides a drill guide device for dental implant to mitigate or obviate the aforementioned problems.

SUMMARY OF THE INVENTION

The main objective of the present invention is to provide a drill guide device for dental implant that can simplify the process and reduce the time for fabricating the surgical stent.

The drill guide device for dental implant comprises a positioning unit and a guiding unit. The positioning unit has a rod, a twist knob and a base. The twist knob is a hemisphere and has a connecting hole formed in a flat end of the twist knob, and the rod is mounted in the connecting hole. The twist knob has a first indexing table around the connecting hole and at least two graduated markings of elevation angle mounted on a curved end of the twist knob. The base has a rotation hole concaved on a top surface of the base, and the rotation hole matches the twist knob. The base has a second indexing table formed around the rotation hole and matches the first indexing table. The twist knob is mounted movably in the rotation hole of the base. The guiding unit is connected to the drill guide device and has an inner guider and a middle guider. The inner guider has a first bending portion, and the cross section of the first bending portion is semi-circular. The inner guider has two first abutting panels formed on two sides of the first bending portion, and an inner diameter of the first bending portion corresponds to an outer diameter of the rod. The middle guider has a second bending portion, and the cross section of the second bending portion is semi-circular, and an inner diameter of the second bending portion corresponds to an outer diameter of the first bending portion. The middle guider has two second abutting panels formed on two sides of the second bending portion. The second abutting panels are respectively attached to the first abutting panels.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
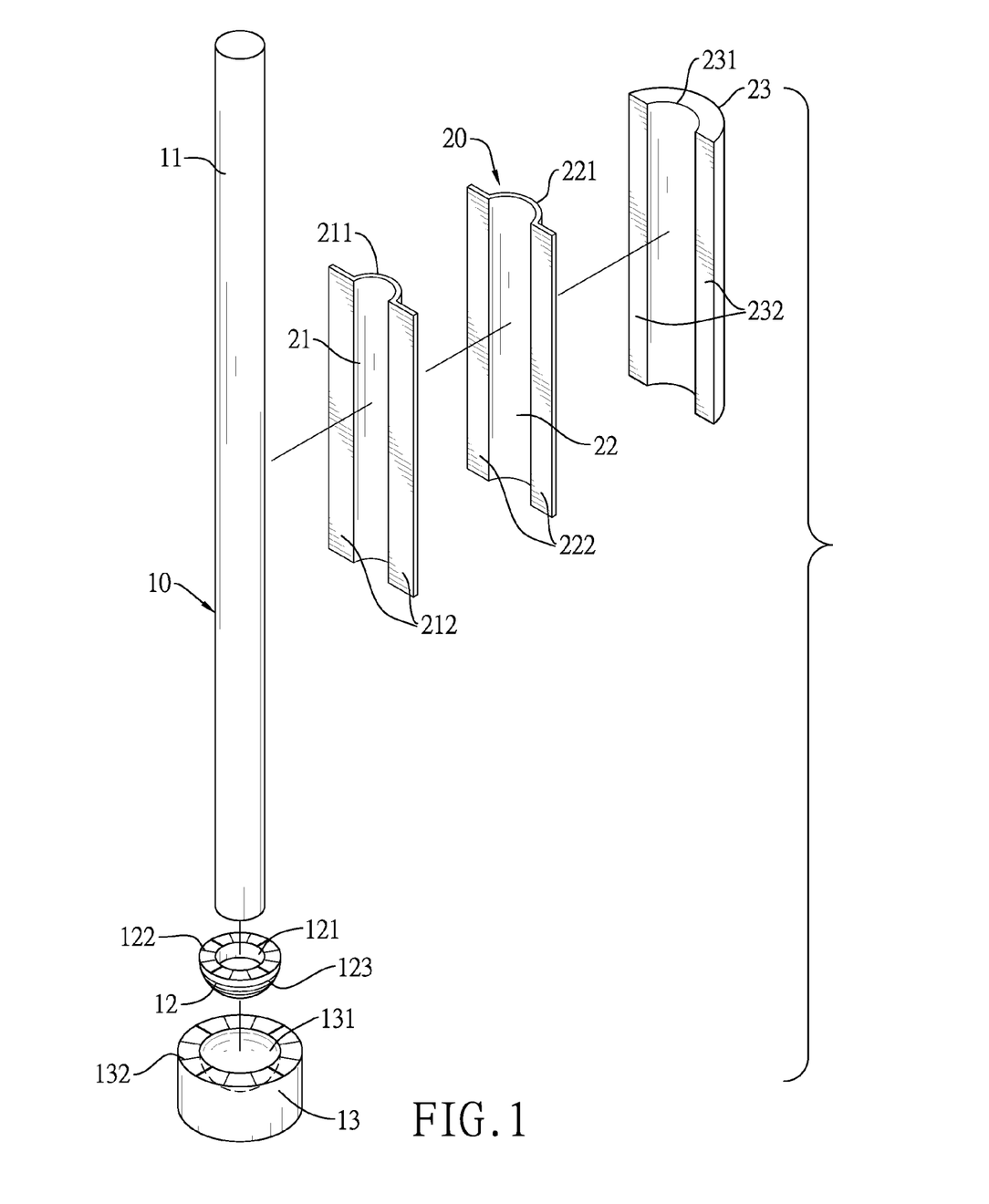
FIG. 1 is an exploded perspective view of a drill guide device for dental implant in accordance with the present invention.

With reference to FIG. 1, a drill guide device for dental implant in accordance with the present invention has a positioning unit 10 and a guiding unit 20.

Figure 1A:
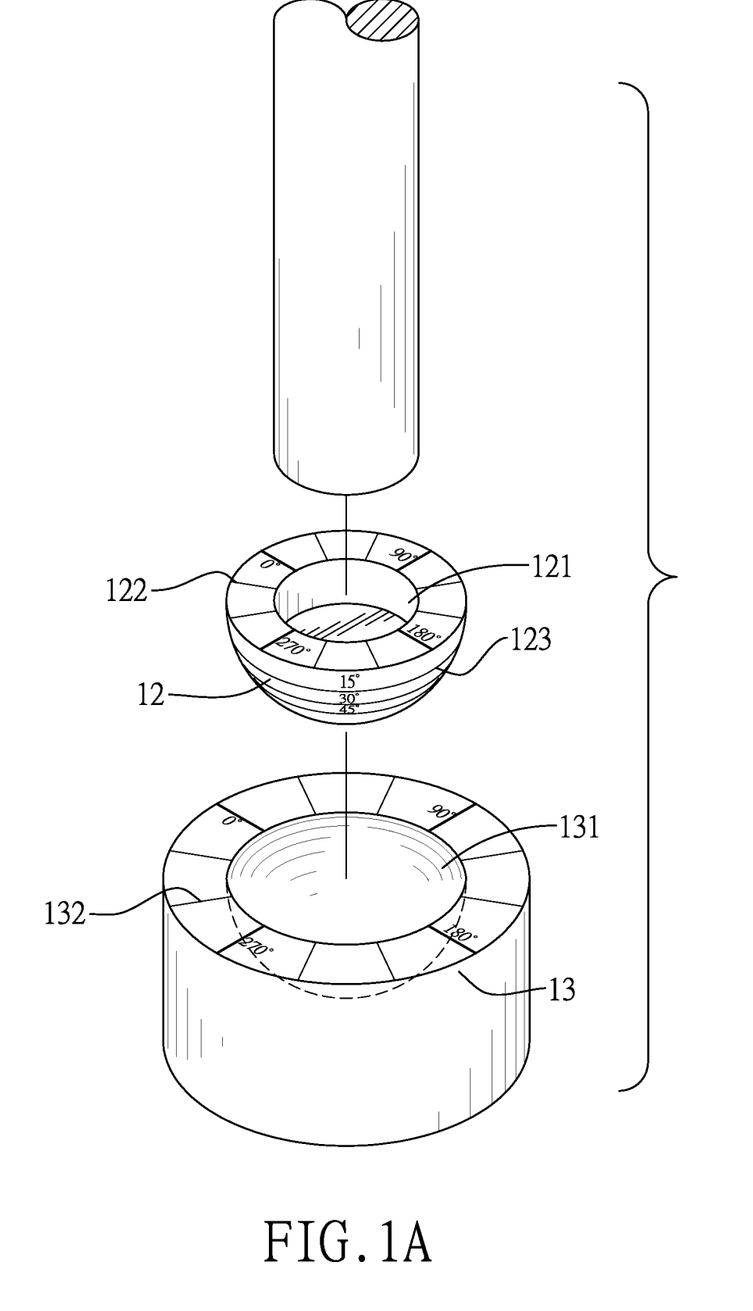
FIG. 1A is an enlarged perspective view of a guiding unit of the drill guide device in FIG. 1.

With reference to FIGS. 1 and 1A, the positioning unit 10 has a rod 11, a twist knob 12 and a base 13. The rod 11 is circular in cross section. The twist knob 12 is a hemisphere and has a flat end, a curved end, a connecting hole 121, a first indexing table 122 and three graduated markings 123 of elevation angle. The connecting hole 121 is formed in the flat end of the twist knob 12, and one end of the rod 11 is mounted in the connecting hole 121 and is encased in the twist knob 12. The first indexing table 122 is mounted on the flat end of the twist knob 12 around the connecting hole 121. The first indexing table 122 has multiple angle symbols such as 0 degree, 90 degrees, 180 degrees and 270 degrees, for further identifying the angulation. Extra angle symbols can be disposed every 15 degrees or every 30 degrees between the angle symbols from 0 degree to 270 degrees of the first indexing table 122. The three graduated markings 123 of elevation angle are formed on the twist knob 12 and include different elevation angles such as 15 degrees, 30 degrees and 45 degrees relative to the curved end of the twist knob 12.

The base 13 is a cylinder and has a rotation hole 131 concaved on a top surface of the base 13, and a depth of the rotation hole 131 matches a curvature of the curved end of the twist knob 12. The base 13 has a second indexing table 132 formed on the base 13 around the rotation hole 131, and the second indexing table 132 matches the first indexing table 122, for example, the angle symbols of 0 degree, 90 degrees, 180 degrees, and 270 degrees. For further identifying the angulation, some extra angle symbols are mounted every 15 degrees or 30 degrees between the angle symbols from 0 degree to 270 degrees. The curved end of the twist knob 12 is mounted movably in the rotation hole 131 of the base 13.

The guiding unit 20 is connected to the positioning unit 10 and has an inner guider 21, a middle guider 22 and an outer cover 23. The inner guider 21 has a first bending portion 211 and two first abutting panels 212. The first bending portion 211 is formed on the inner guider 21, and a cross section of the first bending portion 211 is semi-circular. The first bending portion 211 is attached on the rod 11, in other words, an inner diameter of the first bending portion 211 corresponds to an outer diameter of the rod 11. The first abutting panels 212 are respectively formed on two sides of the first bending portion 211. The middle guider 22 has a second bending portion 221 and two second abutting panels 222. The second bending portion 221 is formed on the middle guider 22, and a cross section of the second bending portion 221 is semi-circular. The second bending portion 221 is attached on the side of the first bending portion 211 that is distal from the rod 11, in other words, an inner diameter of the second bending portion 221 corresponds to an outer diameter of the first bending portion 211. The second abutting panels 222 are respectively formed on two sides of the second bending portion 221 and are attached respectively on the first abutting panels 212.

The outer cover 23 has an arced groove 231 and two abutting surfaces 232. The arced groove 231 is concaved on an inner surface of the outer cover 23 and the two abutting surfaces 232 are located on two sides of the arced groove 231. The arced groove 231 is attached on a side of the second bending portion 221 that is distal from the first bending portion 211, and the two abutting surfaces 232 are respectively attached to the second abutting panels 222.

Figure 2:
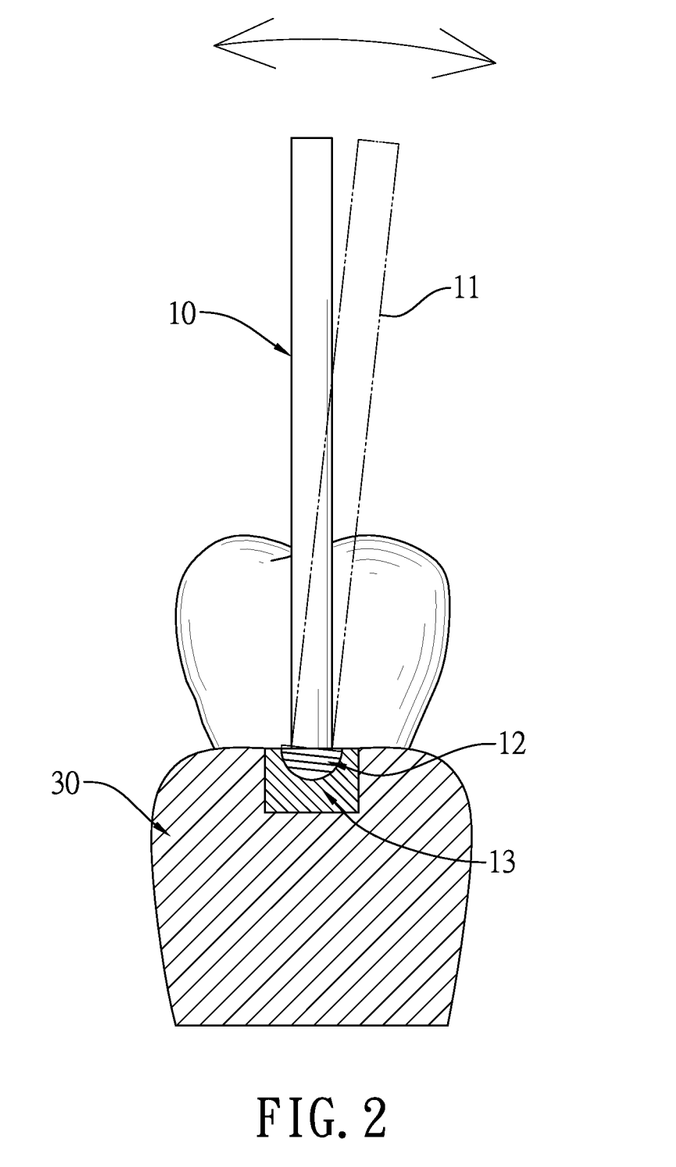
FIG. 2 is an operational side view of the guiding unit in FIG. 1A.
Figure 3:
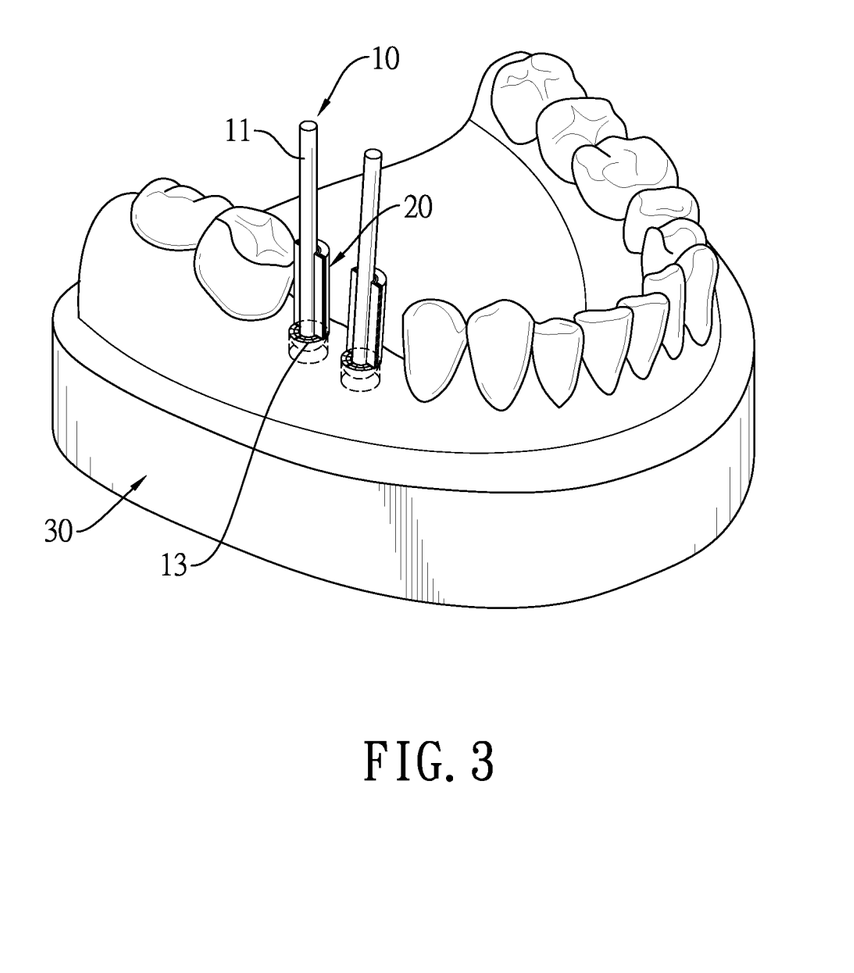
FIG. 3 is an operational perspective view of the drill guide device in FIG. 1, mounted into a gum model.
Figure 4:
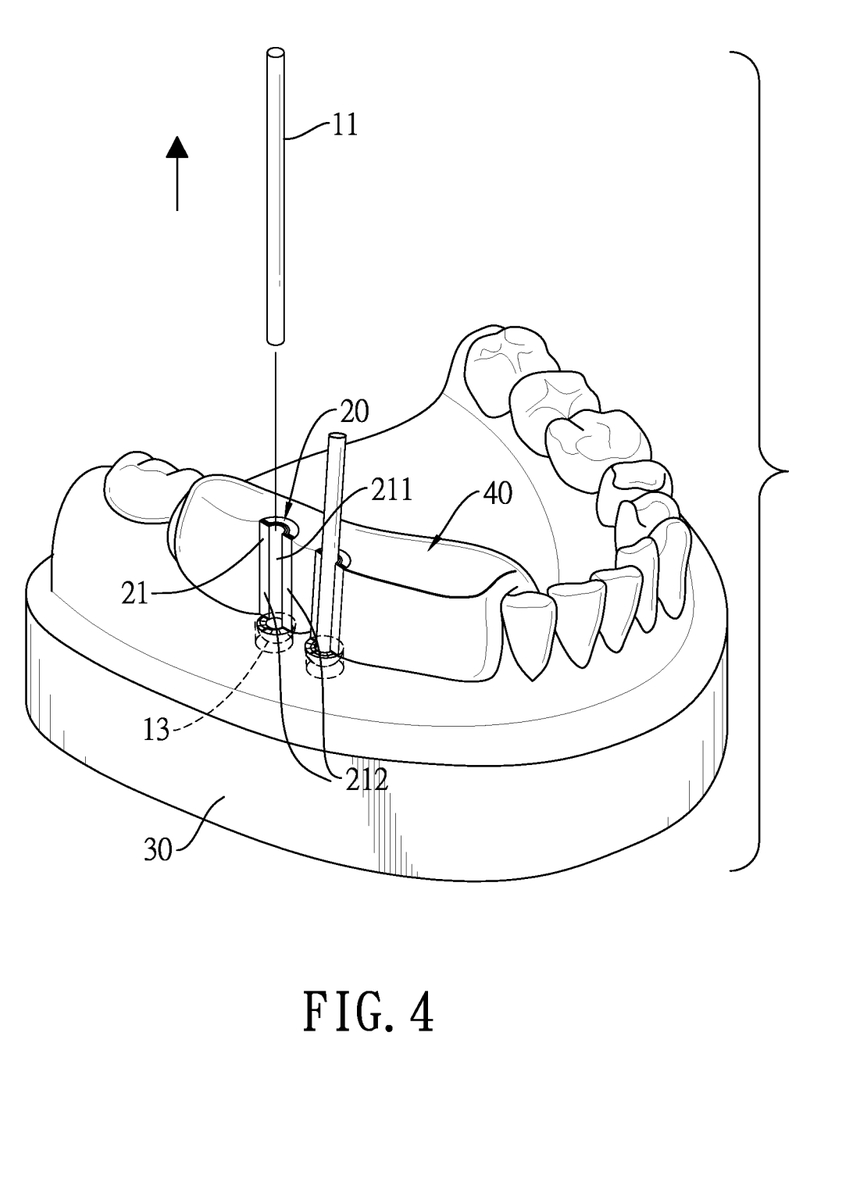
FIG. 4 is an operational perspective view of a surgical stent formed on the gum model in FIG. 3.
Figure 5:
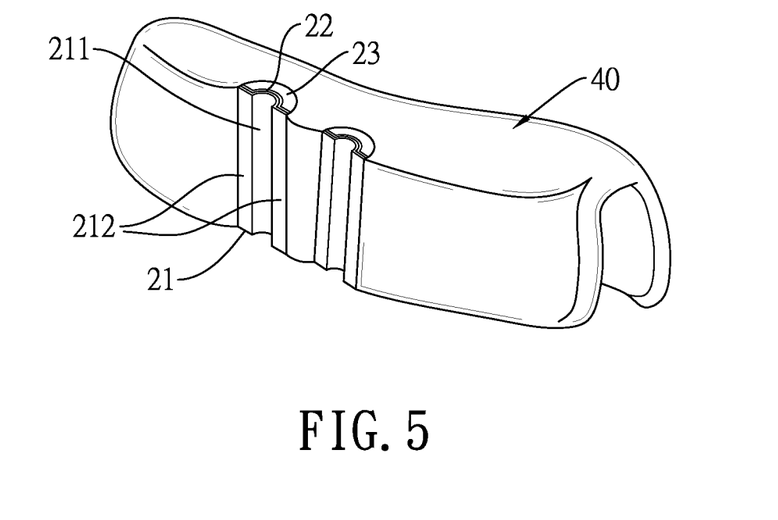
FIG. 5 is a perspective view of the guiding unit and the surgical stent in FIG. 4.

With reference to FIGS. 2 to 4, in use, the locating unit 10 is mounted into a gum model 30 of the patient, and a circular hole of a specific depth is first drilled on an implant site on the gum model 30. Then, the base 13 of the positioning unit 10 is mounted securely in the circular hole of the gum model 30 to fit with a top surface of the gum model 30. The twist knob 12 is mounted into the rotation hole 131 of the base 13, and the first indexing table 122 is adjusted to align with the second indexing table 132, for example, the 0 degree angle symbol of the first indexing table 122 is aligned with the 0 degree angle symbol of the second indexing table 132. In addition, the orientation and elevation angle of the twist knob 12 are adjusted by using the rod 11 to match the oral scan data and the actual diagnosis. After finishing the adjustment of the positioning unit 10, the gum model 30 is double-checked with the oral scan data of the patient, and if the orientation or the elevation angle of the twist knob 12 is incorrect, the orientation and elevation angle of the rod 11 can be re-adjusted. When the readjustment of the positioning unit 10 is finished, the guiding unit 20 is attached to the rod 11, and then the guiding unit 20 and the implant site on the gum model 30 are covered by resin. After a while, the resin is solidified by chemical reaction or light curing machine and is formed into a surgical stent 40.

Figure 6:
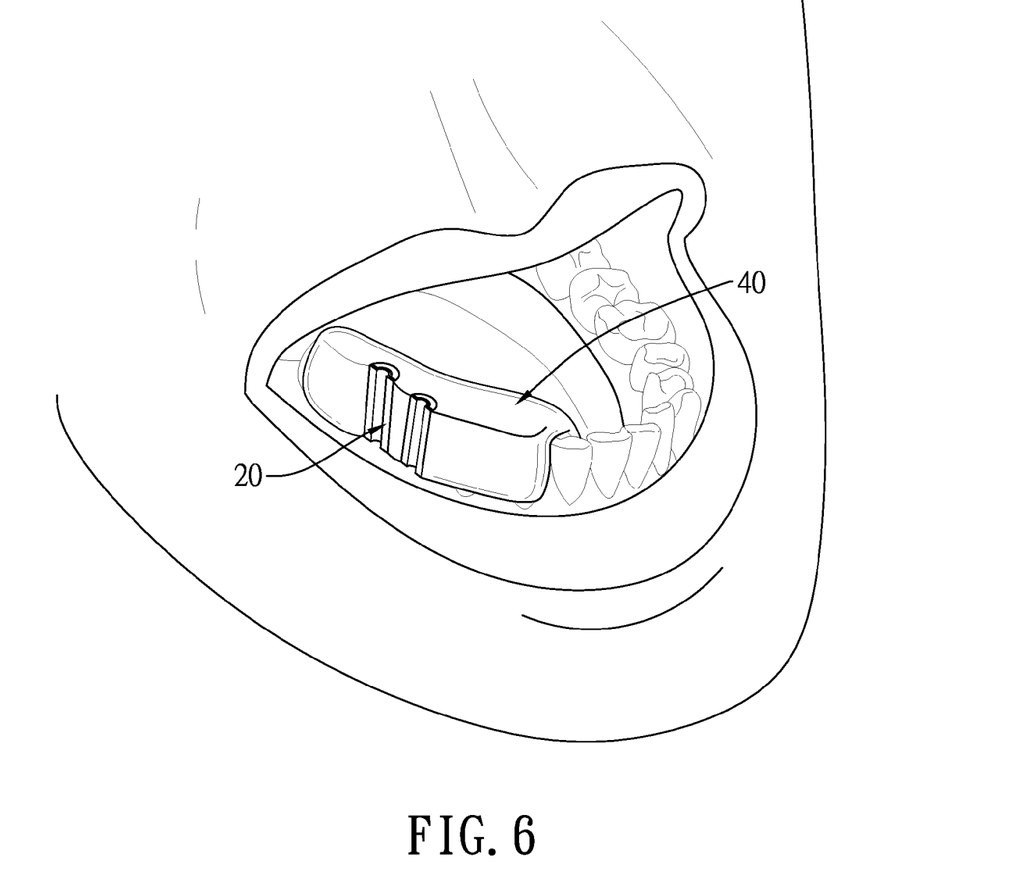
FIG. 6 is an operational perspective view of the surgical stent and the guiding unit in FIG. 5, mounted into a gum of a patient.

With reference to FIGS. 1, 4 and 6, the rod 11 is removed from the twist knob 12, and the guiding unit 20 is located on an outer side of the gum model 30. Then, the surgical stent 40 and the guiding unit 20 are placed in the mouth of the patient corresponding to the implant site, and a drill bit is used to drill a hole in the implant site of the patient along the first bending portion 211 of the inner guider 21. The drill bit is guided by sequentially dismantling the first bending portion 211, the second bending portion 221 and the arced groove 231, and the circular hole in the implant site of the patient is drilled gradually bigger and bigger and finally into a suitable size for planting an implant fixture in the circular hole.

With reference to FIGS. 2 and 3, for fabrication of the surgical stent 40, the pilot hole is first drilled in the implant site of the gum model 30 for accommodating the guiding unit 10. Then the orientation and elevation angle of the rod 11 are adjusted to match the actual diagnosis situation of a patient. The orientation or elevation angel of the rod 11 can be instantly modified when needed, thereby avoiding a waste of time for repairing the circular hole of the gum model.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A drill guide device for dental implant comprising:
   a positioning unit having
      a rod being circular in cross section;
      a twist knob being a hemisphere and encasing one end of the rod; and
      a base being a cylinder, and the twist knob mounted movably in the base;
   a guiding unit having
      an inner guider having
         a first bending portion formed on the inner guider, and the cross section of the first bending portion being semi-circular, the first bending portion attached on the rod, an inner diameter of the first bending portion corresponding to an outer diameter of the rod; and
         two first abutting panels formed on two sides of the first bending portion;
      a middle guider;
         a second bending portion formed on the middle guider, and the cross section of the middle bending portion being semi-circular, the second bending portion attached on the first bending portion, an inner diameter of the second bending portion corresponding to an outer diameter of the first bending portion; and
         two second abutting panels formed on two sides of the second bending portion and respectively attached to the first abutting panels;
   said twist knob including a flat end, a curved end and a connecting hole, the connecting hole formed in the flat end of the twist knob, and one end of the rod mounted in the connecting hole; and
   the base having a rotation hole concaved on a top surface of the base, and a depth of the rotation hole matching a curvature of the curved end of twist knob; and
   said twist knob further including
      a first indexing table mounted on the flat end of the twist knob around the connecting hole; and
      three graduated markings of elevation angle, the markings formed on the curved end of the twist knob; and
   the base including
      a second indexing table formed on the base around the rotation hole and matching the first indexing table.

2. The drill guide device for dental implant as claimed in claim 1, wherein the guiding unit has an outer cover attached to the second bending portion of the middle guider.

3. The drill guide device for dental implant as claimed in claim 1, wherein the guiding unit has an outer cover attached to the second bending portion of the middle guider.

4. The drill guide device for dental implant as claimed in claim 2, wherein the outer cover has
   an arced groove concaved on an inner surface of the outer cover and attached on a side of the second bending portion, as attached to a first bending portion of the middle guider, and said second bending portion is distal from the first bending portion; and
   two abutting surfaces located on two sides of the arced groove and respectively attached to the second abutting panels.

5. The drill guide device for dental implant as claimed in claim 1, wherein the first indexing table has multiple angle symbols including 0 degree, 90 degrees, 180 degrees and 270 degrees; and
   the second indexing table has multiple angle symbols including 0 degree, 90 degrees, 180 degrees and 270 degrees.

6. The drill guide device for dental implant as claimed in claim 1, wherein the three graduated markings include elevation angles of 15 degrees, 30 degrees and 45 degrees relative to the curved end of the twist knob.

\* \* \* \* \*